(12) United States Patent
Takase et al.

(10) Patent No.: US 8,258,333 B2
(45) Date of Patent: Sep. 4, 2012

(54) METHOD FOR PRODUCTION OF N-(2-AMINO-1,2-DICYANOVINYL)IMIDATES, METHOD FOR PRODUCTION OF N-(2-AMINO-1,2-DICYANOVINYL)FORMAMIDINE, AND METHOD FOR PRODUCTION OF AMINOIMIDAZOLE DERIVATIVES

(75) Inventors: Mitsuru Takase, Joetsu (JP); Fuminori Komatsu, Joetsu (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 13/363,062

(22) Filed: Jan. 31, 2012

(65) Prior Publication Data
US 2012/0142957 A1 Jun. 7, 2012

Related U.S. Application Data

(62) Division of application No. 12/450,730, filed as application No. PCT/JP2008/057490 on Apr. 17, 2008.

(30) Foreign Application Priority Data

Apr. 19, 2007 (JP) ................................ 2007-111038
Apr. 19, 2007 (JP) ................................ 2007-111039
Apr. 19, 2007 (JP) ................................ 2007-111041

(51) Int. Cl.
*C07C 257/22* (2006.01)
(52) U.S. Cl. ...................................................... 558/446
(58) Field of Classification Search ........................ None
See application file for complete search history.

(56) References Cited

U.S. PATENT DOCUMENTS 3,778,446 A  12/1973  Weigert
6,797,828 B1  9/2004  Shibasaki et al.

FOREIGN PATENT DOCUMENTS

| EP | 1 215 206 A1 | 6/2002 |
| JP | A-2001-151760 | 6/2001 |
| JP | A-2001-158776 | 6/2001 |
| JP | A-2001-302609 | 10/2001 |
| JP | A-2002-155059 | 5/2002 |
| JP | A-2003-246779 | 9/2003 |
| WO | WO 01/21592 A1 | 3/2001 |
| WO | WO 2004/035529 A1 | 4/2004 |

OTHER PUBLICATIONS

Jansson et al.; "Solid-Phase Synthesis and Characterization of 0-Dimannosylated Heptadecapeptide Analogues of Human Insulin-like Growth Factor 1 (IGF-1);" *J. Chem Soc. Perkin Trans.*; 1992; pp. 1699-1707.
Booth et al; "Synthesis of 9-Hydroxyalkyl-substituted Purines from the Corresponding 4-(C-Cyanoformimidoyl) imidazole-5-amines;" *J. Chem. Soc. Perkin Trans*; 1992; pp. 2119-2125.
Booth et al.; "Synthesis of {1α, 2β, 3α-2,3-bis(benzyloxymethyl)cyclobutyl]imidazol-5-amines: important precursors to Cyclobut-A derivatives;" *J. Chem. Soc. Perkin Trans*; 1995; pp. 669-675.
Johnson et al; "1-Alkylation of 4,5-Dicyanoimidazole by Ortho Esters;" *Synthesis*; 1991; pp. 75-78.
Alves; "Synthesis of 5-Amino-4-(cyanoformimidoyl)-1H-imidazole:a Reactive Intermediate for the Synthesis of 6-Carbamoyl-1, 2-dihydropurines and 6-Carbamoylpurines;" *J. Chem. Soc. Perkin Trans*; 1990; pp. 1705-1712.
May 10, 2010 European Search Report Issued in European Application No. 08 74 0560.
Jul. 8, 2008 International Search Report Issued in International Application No. PCT/JP2008/057490.

*Primary Examiner* — Michael Barker
(74) *Attorney, Agent, or Firm* — Oliff & Berridge, PLC

(57) ABSTRACT

A method for producing N-(2-amino-1,2-dicyanovinyl)formamidine, including the steps of reacting an N-(2-amino-1,2-dicyanovinyl)formimidate and ammonia by adding aqueous ammonia to a solution or suspension of an N-(2-amino-1,2-dicyanovinyl)formimidate in ether, or alternatively directly adding an N-(2-amino-1,2-dicyanovinyl)formimidate or adding a solution or suspension of an N-(2-amino-1,2-dicyanovinyl)formimidate in ether to a liquid containing ether and aqueous ammonia.

2 Claims, No Drawings

METHOD FOR PRODUCTION OF N-(2-AMINO-1,2-DICYANOVINYL)IMIDATES, METHOD FOR PRODUCTION OF N-(2-AMINO-1,2-DICYANOVINYL)FORMAMIDINE, AND METHOD FOR PRODUCTION OF AMINOIMIDAZOLE DERIVATIVES

CROSS-REFERENCE TO PRIOR APPLICATIONS

This is a divisional of application Ser. No. 12/450,730 filed Oct. 9, 2009, which is a National Stage Application of PCT/JP2008/057490 filed Apr. 17, 2008, and claims the benefit of Japanese Patent Application Nos. 2007-111038, 2007-111039, and 2007-111041 all of which were filed on Apr. 19, 2007. The entire disclosures of the prior applications are hereby incorporated by reference herein in their entirety.

TECHNOLOGICAL FIELD

The first mode of the present invention relates to a method for producing N-(2-amino-1,2-dicyanovinyl)imidates. More particularly, it relates to a method for producing N-(2-amino-1,2-dicyanovinyl)imidates (hereinafter, referred to as RMD in some cases) represented by the following formula (1-III) under low temperature conditions within a short period of time in high yield.

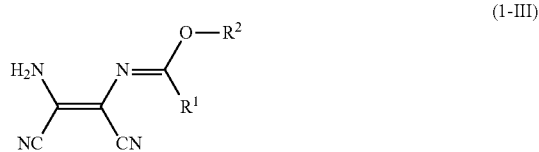

(1-III)

In formula (1-III), $R^1$ is a hydrogen atom, an optionally substituted alkyl group, or an optionally substituted aryl group; and $R^2$ is an optionally substituted alkyl group, or an optionally substituted aryl group.

The second mode of the present invention relates to a method for producing N-(2-amino-1,2-dicyanovinyl)formamidine (hereinafter, referred to as AMD-H in some cases). More particularly, it relates to a method for producing N-(2-amino-1,2-dicyanovinyl)formamidine represented by the following formula (2-II) which enhances yield of a cyclization reaction for producing 5-amino-1H-imidazole-4-carboxamide (hereinafter, referred to as AICA in some cases), 5-amino-1H-imidazole-4-carbonitrile (hereinafter, referred to as AICN in some cases), or the like.

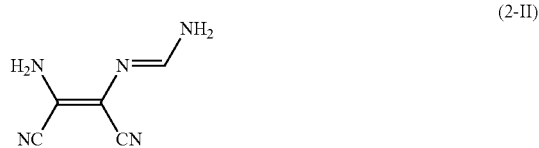

(2-II)

The third mode of the present invention relates to a method for producing aminoimidazole derivatives. More particularly, it relates to a method for producing aminoimidazole derivatives represented by the following formula (3-V) in high yield by using diaminomaleonitrile as a starting substance.

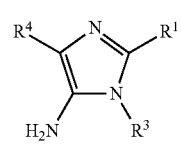

(3-V)

In formula (3-V), each of $R^1$ and $R^3$ is independently a hydrogen atom, an optionally substituted alkyl group, or an optionally substituted aryl group; and $R^4$ is —CN or —CONH$_2$.

BACKGROUND ART

Methyl N-(2-amino-1,2-dicyanovinyl)formimidate, which is one type of the RMDs according to the first mode of the present invention, is a useful material of an intermediate for producing AICN which is a precursor of urazamide of a hepatoprotective drug, dacarbazine and temozoromide of antineoplastic drugs, or producing 4,5-dicyanoimidazole (hereinafter, referred to as DCI in some cases).

As a method for synthesizing RMD, Non-Patent Document 1 describes a method for synthesizing ethyl N-(2-amino-1,2-dicyanovinyl)formimidate (hereinafter, referred to as EMD in some cases) by reacting diaminomaleonitrile (hereinafter, referred to as DAMN in some cases) and triethyl orthoformate in dioxane at a high temperature.

In addition, Patent Document 1 discloses a method for producing an alkyl N-(2-amino-1,2-dicyanovinyl)formimidate characterized by reacting diaminomaleonitrile and a trialkyl orthoformate in an alcohol having 1 to 5 carbon atoms by means of heating and refluxing.

It is known that under high temperature conditions, DAMN is decomposed or a polymerization reaction occurs. Even in the aforementioned production methods, by-products are produced by side reactions of the aforementioned DAMN. In addition, RMDs are easily decomposed under high temperature conditions. For this reason, even if an RMD is produced in accordance with the aforementioned production method, a part of the RMD is decomposed. Therefore, development of a method in which RMD can be synthesized within a short period of time under low temperature conditions is desirable.

On the other hand, it is known that AICN or AICA which is an intermediate of medicine can be obtained by amidinating an RMD to form an N-(2-amino-1,2-dicyanovinyl)formamidine (hereinafter, referred to as AMD in some cases), subsequently carrying out a cyclization reaction and a hydrolysis reaction in a basic aqueous solution (for example, see Patent Document 2). Increasing the efficiencies of the aforementioned cyclization reaction and hydrolysis reaction and enhancing yield of AICN and AICA are desirable. A method for producing an RMD which is a raw material of AMD used in the aforementioned cyclization reaction may effect efficiency of the cyclization reaction or the like. For this reason, it is important that the method for producing the RMD complies with the cyclization reaction.

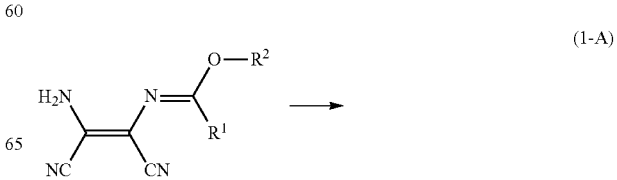

(1-A)

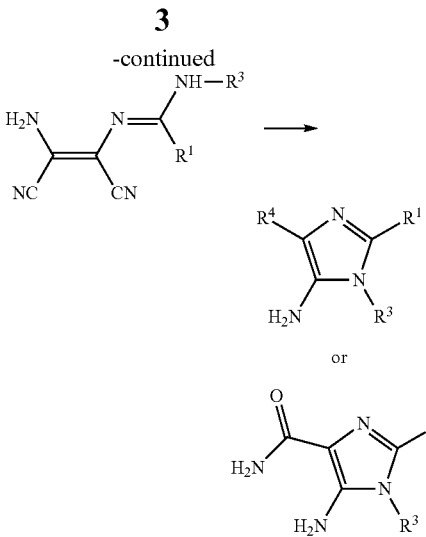

or

N-(2-amino-1,2-dicyanovinyl)formamidine of the second mode of the present invention is a useful raw material of an intermediate for producing DCI, AICN or AICA which is a precursor of urazamide of a hepatoprotective drug, or dacarbazine and temozoromide of antineoplastic drugs.

Examples of synthesis methods for AMD-H include a method in which AMD-His obtained by a one-step reaction from diaminomaleonitrile and a method in which AMD-His obtained by a two-step reaction from diaminomaleonitrile.

As the one-step synthesis method, for example, Non-Patent Document 1 discloses a method in which DAMN and formamidine acetate are heated to refluxing temperature in ethanol. However, the yield thereof is only 2%.

Patent Document 2 and Patent Document 3 disclose a method in which diaminomaleonitrile, hydrogen chloride, and isobutyronitrile or hydrogen cyanide are reacted in an organic solvent.

In addition, Patent Document 4 discloses a method in which diaminomaleonitrile, formamide and phosphorous oxychloride are reacted in a solvent such as tetrahydrofuran.

On the other hand, as the two-step synthesis method, for example, Non-Patent Document 2 discloses a method in which diaminomaleonitrile and triethyl orthoformate are reacted in dioxane at a high temperature to synthesize EMD, and EMD and ammonia are reacted in chloroform with aniline hydrochloride as a catalyst at a temperature of not more than −20° C.

In addition, Patent Document 1 discloses a method in which diaminomaleonitrile and a trialkyl orthoformate are heated and refluxed in an alcohol having 1 to 5 carbon atoms to synthesize an alkyl N-(2-amino-1,2-dicyanovinyl)formimidate, and the alkyl N-(2-amino-1,2-dicyanovinyl)formimidate is reacted with ammonia in an alcohol having 1 to 5 carbon atoms.

In addition, Patent Document 5 discloses, as examples of a method of producing AMD-H by reacting an RMD represented by a compound shown by the following formula (2-I) and ammonia, (1) a method in which an ammonia gas is blown into a solution or suspension of RMD in an alcohol having 1 to 5 carbon atoms, (2) a method in which an ammonia gas is blown into an alcohol having 1 to 5 carbon atoms to dissolve ammonia therein, followed by directly adding RMD thereto or adding a solution or suspension of RMD in an alcohol having 1 to 5 carbon atoms thereto, (3) a method in which a solution or suspension of RMD in an alcohol having 1 to 5 carbon atoms is added to ammonia condensed at a low temperature, (4) a method in which an aqueous ammonia is used instead of using the ammonia gas in the aforementioned method (1) or (2), and the like.

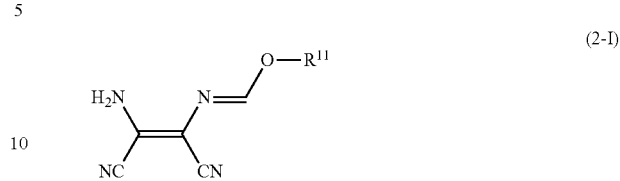

In formula (2-I), $R^{11}$ is an optionally substituted alkyl group, or an optionally substituted aryl group.

On the other hand, it is known that AICN or AICA which is an intermediate of medicine can be obtained by amidinating RMD to obtain N-(2-amino-1,2-dicyanovinyl)formamidine, followed by subjecting to a cyclization reaction and a hydrolysis reaction in a basic aqueous solution (for example, see Patent Document 2). Increasing the efficiencies of the aforementioned cyclization reaction and hydrolysis reaction and enhancing the yields of AICN and AICA are desirable. A method for producing AMD-H used in the aforementioned cyclization reaction may effect efficiency of the cyclization reaction or the like. For this reason, it is important that the method for producing AMD-H complies with the cyclization reaction.

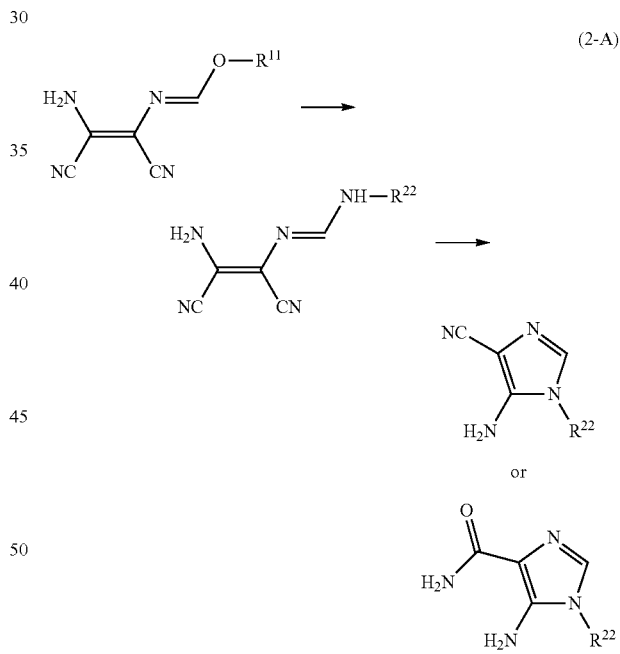

AICA or AICN which is one type of aminoimidazole derivatives represented by formula (3-V) according to the third mode of the present invention is a useful raw material of an intermediate for producing urazamide of a hepatoprotective drug, and dacarbazine and temozoromide of antineoplastic drugs.

As a synthesis method for the aminoimidazole derivatives represented by formula (3-V), for example, a method in which 4-nitroimidazole-5-carboxamide is subjected to a catalytic reduction, a method in which phenylazomalonamidine is subjected to a reductive ring closure, a method in which α-amino-α-cyanoacetamide is used as a raw material, a method in which a compound having a purine nucleus is decomposed, and the like are known. However, the aforementioned methods have drawbacks for industrial use in view of easy availability or easiness of operation.

A method is known in which 4,5-dicyanoimidazole is synthesized from DAMN easily available as an industrial raw material (Japanese Examined Patent Application, Second Publication No. S46-4373), followed by hydrolyzing the compound (Japanese Examined Patent Application, Second Publication No. S41-21026) to synthesize 5-cyano-1H-imidazole-4-carboxamide, and the obtained compound is subjected to a Hofmann rearrangement reaction to convert into 5-amino-1H-imidazole-4-carbonitrile, followed by hydrolyzing the obtained compound to synthesize 5-amino-1H-imidazole-4-carboxamide. However, in the aforementioned synthesis method, yield is low.

Non-Patent Document 1 reports that AICN can be synthesized by ring-closing N-(2-amino-1,2-dicyanovinyl)formamidine. In addition, Non-Patent Document 2 and Non-Patent Document 3 report that a 1-substituted-5-aminoimidazole-4-carbonitrile can be synthesized by ring-closing an N-(2-amino-1,2-dicyanovinyl)-N'-substituted-formamidine.

Patent Document 3 and Patent Document 2 disclose that diaminomaleonitrile, hydrogen chloride, and isobutyronitrile or hydrogen cyanide are reacted in an organic solvent to obtain AMD, and the AMD is subjected to a cyclization reaction in an aqueous solution of sodium hydroxide to synthesize AICN or AICA. In addition, Patent Document 4 discloses that diaminomaleonitrile, formamide and phosphorous oxychloride are reacted in a solvent such as tetrahydrofuran to obtain AMD, and an aqueous solution or aqueous suspension of the obtained AMD is reacted with a basic compound to synthesize AICN. In addition, Patent Document 6 discloses a method in which AMD is cyclized and hydrolyzed in a basic aqueous solution to synthesize AICA.

Patent Document 1: Japanese Unexamined Patent Application, First Publication No. 2001-302609
Patent Document 2: WO 2004/035529
Patent Document 3: Japanese Unexamined Patent Application, First Publication No. 2001-158776
Patent Document 4: Japanese Unexamined Patent Application, First Publication No. 2002-155059
Patent Document 5: WO 2001/21592
Patent Document 6: Japanese Unexamined Patent Application, First Publication No. 2001-151760
Non-Patent Document 1: B. L. Booth et al., J. Chem. Soc. Perkin Trans. I, 1990, 1705
Non-Patent Document 2: B. L. Booth et al., J. Chem. Soc. Perkin Trans. I, 1992, 2120
Non-Patent Document 3: B. L. Booth et al., J. Chem. Soc. Perkin Trans. I, 1995, 669

DISCLOSURE OF THE INVENTION

Problems to be Solved by the Invention

An objective of the first mode of the present invention is to provide a method for producing N-(2-amino-1,2-dicyanovinyl)imidates under low temperature conditions within a short period of time in high yield.

An objective of the second mode of the present invention is to provide a method for producing N-(2-amino-1,2-dicyanovinyl)formamidine which well complies with a cyclization reaction for producing AICN, AICA and the like, and enhances the yields thereof.

An objective of the third mode of the present invention is to provide a method for producing aminoimidazole derivatives represented by formula (3-V) by cyclizing a compound represented by the following formula (3-IV) and/or a salt thereof, in high yield.

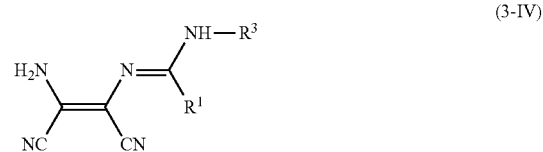

In formula (3-IV), each of $R^1$ and $R^3$ is independently a hydrogen atom, an optionally substituted alkyl group, or an optionally substituted aryl group.

Another objective of the third mode of the present invention is to provide a method for producing aminoimidazole derivatives represented by formula (3-V) in high yield using diaminomaleonitrile as a starting substance.

Means for Solving the Problems

As a result of diligent studies in order to achieve the objective of the first mode of the present invention, the present inventors discovered that an N-(2-amino-1,2-dicyanovinyl) imidate can be obtained under low temperature conditions within a short period of time by reacting diaminomaleonitrile and a triester orthoformate or the like in the presence of a strong acid such as sulfuric acid. The first modes of the present invention were completed as a result of further diligent studies on the basis of the aforementioned finding.

The first modes of the present invention further include the following modes.

(1) A method for producing N-(2-amino-1,2-dicyanovinyl) imidates comprising the step of reacting diaminomaleonitrile with a compound represented by the following formula (1-II):

$$CR^1(OR^2)_3 \qquad (1\text{-}II)$$

wherein $R^1$ is a hydrogen atom, an optionally substituted alkyl group, or an optionally substituted aryl group; and each $R^2$ is independently an optionally substituted alkyl group, or an optionally substituted aryl group, in the presence of a strong acid.

(2) The aforementioned method for producing N-(2-amino-1,2-dicyanovinyl)imidates wherein the strong acid is trifluoroacetic acid, methanesulfonic acid, p-toluenesulfonic acid or concentrated sulfuric acid.

(3) The aforementioned method for producing N-(2-amino-1,2-dicyanovinyl)imidates wherein the compound represented by formula (1-II) is a triester orthoformate or a triester orthoacetate.

(4) The aforementioned method for producing N-(2-amino-1,2-dicyanovinyl)imidates wherein the aforementioned reaction is carried out in an aprotic organic solvent.

(5) The aforementioned method for producing N-(2-amino-1,2-dicyanovinyl)imidates wherein the aforementioned aprotic organic solvent is tetrahydrofuran.

As a result of further studies in order to achieve the objective of the second mode of the present invention, the present inventors discovered that when AMD-H obtained by reacting RMD and ammonia in an alcohol as described in Patent Document 1 and Patent Document 5 is used in a cyclization reaction for producing AICN, AICA and the like, by-products are produced due to non-preferable reactions or the like, and the production of AICN, AICA and the like in high purity is inhibited.

The present inventors further discovered that when AMD-H obtained by reacting RMD and ammonia in ether is used, side reactions can be controlled during the cyclization reaction. However, an ammonia gas has poor solubility in ether represented by tetrahydrofuran, and for this reason, lines of a reactor are easily blocked, and use of an ammonia gas is disadvantageous in industrial production. Therefore, the present inventors discovered that by means of adding aqueous ammonia to a solution or suspension of RMD in ether, or alternatively adding RMD per se or a solution or suspension of RMD in ether to a liquid containing aqueous ammonia and ether to react RMD and ammonia, AMD-H which is accompanied with a cyclization reaction for producing AICN, AICA and the like and enhances the yields thereof can be produced. The second modes of the present invention were completed as a result of further studies on the basis of the aforementioned finding.

The second modes of the present invention further contain the following modes.

(1) A method for producing N-(2-amino-1,2-dicyanovinyl)formamidine, comprising the steps of adding aqueous ammonia to a solution or suspension of an N-(2-amino-1,2-dicyanovinyl)formimidate in ether, or alternatively directly adding an N-(2-amino-1,2-dicyanovinyl)formimidate or adding a solution or suspension of an N-(2-amino-1,2-dicyanovinyl)formimidate in ether to a liquid containing ether and aqueous ammonia, to react an N-(2-amino-1,2-dicyanovinyl)formimidate and ammonia.

(2) The aforementioned method for producing N-(2-amino-1,2-dicyanovinyl)formamidine, wherein the aforementioned ether is tetrahydrofuran.

As a result of diligent studies in order to achieve the aforementioned objective of the third mode of the present invention, the present inventors discovered that in step (C) of cyclizing a compound represented by formula (3-IV) and/or a salt thereof in the presence of a basic aqueous solution, when a large amount of an aprotic organic solvent such as alcohol or the like is used, by-products are easily produced and increasing the yield is limited. Therefore, the present inventors discovered that in step (C) of cyclizing a compound represented by formula (3-IV) and/or a salt thereof in the presence of a basic aqueous solution, when an aprotic organic solvent is used, production of by-products is greatly reduced, and an aminoimidazole derivative represented by formula (3-V) can be obtained in high yield.

In addition, the present inventors discovered that in all of step (A) of reacting diaminomaleonitrile and a compound represented by formula (3-I) in the presence of a strong acid to obtain a compound represented by formula (3-II), step (B) of reacting a compound represented by formula (3-II) and a compound represented by formula (3-III) to obtain a compound represented by formula (3-VI) and/or a salt thereof, and step (C) of cyclizing a compound represented by formula (3-VI) and/or a salt thereof in the presence of a basic aqueous solution, by means of using an aprotic organic solvent, an aminoimidazole derivative can be synthesized from diaminomaleonitrile in one pot within a short period of time in high yield. The third mode of the present invention was completed as a result of further studies on the basis of the aforementioned finding.

The third modes of the present invention further contain the following modes.

(1) A method for producing aminoimidazole derivatives represented by the following formula (3-V), comprising carrying out step (C) of cyclizing a compound represented by the following formula (3-IV) and/or a salt thereof in the presence of a basic aqueous solution, in the presence of an aprotic organic solvent.

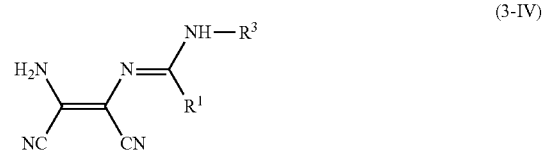

(3-IV)

In formula (3-IV), each of $R^1$ and $R^3$ is independently a hydrogen atom, an optionally substituted alkyl group, or an optionally substituted aryl group.

(3-V)

In formula (3-V), $R^1$ and $R^3$ represent the same meanings as defined in formula (3-IV); and $R^4$ is —CN or —CONH$_2$.

(2) A method for producing aminoimidazole derivatives represented by the following formula (3-VIII) comprising carrying out all of step (A) of reacting diaminomaleonitrile and a compound represented by the following formula (3-I) in the presence of a strong acid to obtain a compound represented by the following formula (3-II),

(3-I)

in formula (3-I), $R^{31}$ is a hydrogen atom; and each $R^{32}$ is independently an optionally substituted alkyl group, or an optionally substituted aryl group.

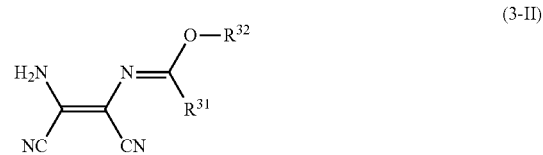

(3-II)

in formula (3-II), $R^{31}$ and $R^{32}$ represent the same meanings as defined in formula (3-I), step (B) of reacting a compound represented by formula (3-II) and a compound represented by formula (3-III) to obtain a compound represented by formula (3-VI) and/or a salt thereof,

(3-III)

in formula (3-III), $R^3$ is a hydrogen atom, an optionally substituted alkyl group, or an optionally substituted aryl group,

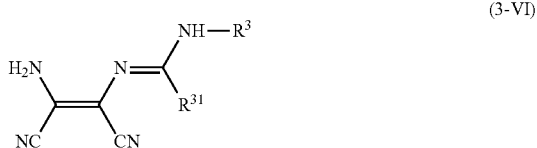

(3-VI)

in formula (3-VI), $R^{31}$ represents the same meaning as defined in formula (3-I); and $R^3$ represents the same meaning as defined in formula (3-III), and step (C) of cyclizing a compound represented by formula (3-VI) and/or a salt thereof in the presence of a basic aqueous solution, in the presence of an aprotic organic solvent.

(3-VIII)

In formula (3-VIII), $R^{31}$ represents the same meaning as defined in formula (3-I); $R^3$ represents the same meaning as defined in formula (3-III); and $R^4$ is —CN or —CONH$_2$.

(3) The aforementioned method for producing aminoimidazole derivatives, wherein the strong acid is trifluoroacetic acid, methanesulfonic acid, p-toluenesulfonic acid, or condensed sulfuric acid.

(4) The aforementioned method for producing aminoimidazole derivatives, wherein step (B) is carried out by mixing a solution or suspension of the aforementioned compound represented by formula (3-II) in an aprotic organic solvent and an aqueous solution of the compound represented by formula (3-III).

(5) The aforementioned method for producing aminoimidazole derivatives, wherein the aforementioned aprotic organic solvent is tetrahydrofuran.

EFFECTS OF THE INVENTION

In accordance with the production method of the first mode of the present invention, an N-(2-amino-1,2-dicyanovinyl)imidate (RMD) can be obtained under low temperature conditions within a short period of time in high yield. In addition, the RMD obtained in accordance with the method of the first mode of the present invention can carry out an amidination reaction, cyclization reaction and hydrolysis reaction in high efficiencies. For this reason, the RMD is useful as a synthesis raw material of an intermediate of medicine such as AICN.

In accordance with the production method of the second mode of the present invention, AMD-H can be efficiently obtained. In addition, the AMD-H obtained in accordance with the method of the second mode of the present invention can control side reactions in a cyclization reaction and a hydrolysis reaction, and cyclization can be carried out in high efficiency. For this reason, the AMD-H is useful as a synthesis raw material of an intermediate of medicine such as AICN.

In accordance with the production method of the third mode of the present invention, by-products are greatly reduced, and aminoimidazole derivatives represented by formula (3-V) can be obtained in high yield. In the production method for the third mode of the present invention, the solvent used in all of the steps until obtaining the aminoimidazole derivatives represented by formula (3-V) from diaminomaleonitrile, which is a starting material, can be an aprotic organic solvent. Therefore, the aminoimidazole derivatives represented by formula (3-V) can be synthesized from diaminomaleonitrile in one pot within a short period of time in high yield.

BEST MODES FOR CARRYING OUT THE INVENTION

Best Modes for Carrying Out the First Modes of the Present Invention $R^1$ in formula (1-II) is a hydrogen atom, an optionally substituted alkyl group, or an optionally substituted aryl group.

As examples of the optionally substituted alkyl group, mention may be made of a methyl group, an ethyl group, a n-propyl group, an isopropyl group, a n-butyl group, an isobutyl group, a t-butyl group, a pentyl group, a hexyl group, a n-decyl group, a methoxymethyl group, a methylthiomethyl group, a 4-acetoxy-3-acetoxymethyl-butyl group, a hydroxyethyl group, a 2-hydroxypropyl group, a 4-hydroxy-3-hydroxymethyl-butyl group, a 2-hydroxyethoxymethyl group, a 2-hydroxy-1-hydroxymethyl-ethoxymethyl group, a 4-hydroxy-2-hydroxymethyl-butyl group, a 5-(N-methylcarbamoyloxy)butyl group, a hydroxycarbonylmethyl group, a 2-chloroethyl group, a 2-dimethylaminoethyl group, an N-substituted-2-asparagyl group, and the like.

As examples of the optionally substituted aryl group, mention may be made of a phenyl group, a 4-methylphenyl group, a 4-chlorophenyl group, a 2,3-dimethylphenyl group, a 3,5-dimethylphenyl group, a 2,6-dimethylphenyl group, a 4-methoxyphenyl group, a 3-phenoxyphenyl group, a 4-phenylphenyl group, a 4-(2-chlorophenyl)phenyl group, 4-(3-isooxazolylphenyl)phenyl group, a 3-benzylphenyl group, a 2-pyridylmethylphenyl group, and the like. Among these, $R^1$ is preferably a hydrogen atom in view of efficiency of the amidination reaction. When $R^1$ is a methyl group or a phenyl group, production of dicyanoimidazole derivatives preferentially occurs at the time of the cyclization reaction.

Each $R^2$ in formula (1-II) is independently an optionally substituted alkyl group, or an optionally substituted aryl group. As examples of an optionally substituted alkyl group or examples of an optionally substituted aryl group in $R^2$, mention may be made of the same examples as described in the aforementioned $R^1$. All $R^2$s in formula (1-II) may be the same or different. In accordance with the production method of the first mode of the present invention, an alcohol ($R^2$OH) derived from $R^2$ in formula (1-II) is by-produced. As $R^2$, an alkyl group having 1 to 5 carbon atoms is preferable, and a methyl group or an ethyl group is most preferable, since the alcohol as a by-product is easily removed efficiently.

The reaction is carried out using the compound represented by formula (1-II) in an amount usually ranging from 1 to 2 equivalents, and preferably ranging from 1.05 to 1.3 equivalents with respect to DAMN. With the usage amount within the aforementioned range, the side reaction is reduced and production cost can be reduced.

The strong acid used in the production method of the first mode of the present invention is an acid almost completely ionized in an aqueous solution. As examples thereof, mention may be made of sulfuric acid, hydrobromic acid, hydroiodic acid, nitric acid, hydrochloric acid, perchloric acid, methanesulfonic acid, p-toluenesulfonic acid, trifluoroacetic acid, trifluoromethanesulfonic acid and the like. A weak acid such as carbonic acid, acetic acid, boric acid, hydrogen sulfide or the like is not suitable for the production method of the first mode of the present invention. The usage amount of the strong acid preferably ranges from 0.2 to 0.5% by mol with respect to DAMN. If the amount of the strong acid is increased much, the amount of by-products tends to be increased.

In the production method of the first mode of the present invention, a solvent can be suitably used. The amount of the solvent usually ranges from 0 to 1 L and preferably ranges from 0.1 to 0.3 L with respect to one mol of DAMN. As examples of the solvent, mention may be made of an ether such as tetrahydrofuran, dioxane, diethyl ether, diethylene glycol dimethyl ether or the like; an alcohol such as methanol, ethanol, n-propanol, isopropanol, n-butanol, isobutanol, t-butanol or the like; and other organic solvents. Among these, an aprotic organic solvent is preferable and an ether is more preferable, and in particular, tetrahydrofuran is preferable, in view of increased efficiency of the amidination reaction, cyclization reaction and hydrolysis reaction using the obtained RMD liquid.

In the production method of the first mode of the present invention, the strong acid may be present in the reaction between DAMN and the compound represented by formula (1-II), and addition order of the synthesis raw materials, addition rate and the like are not particularly limited. In the production method of the first mode of the present invention, usually, the solvent, DAMN and the compound represented by formula (1-II) in specified amounts are first placed in a reactor once or separately, and subsequently, the strong acid is added thereto. After the strong acid is added, the reaction system is maintained at a specified temperature, and the reaction is carried out.

The reaction temperature is not particularly limited. If the reaction temperature is remarkably reduced, the reaction slowly proceeds, and a long period of time is needed for production. In contrast, if the reaction temperature is remarkably increased, an amount of by-products such as 4,5-dicyanoimidazole and the like is increased, and purity tends to be reduced. Therefore, the reaction temperature usually ranges from room temperature (around 20° C.) to the reflux temperature of the solvent, and preferably ranges from 30 to 50° C. In addition, the reaction period is preferably within one hour. If the reaction period is remarkably long, the amount of by-products is increased, and purity tends to be reduced.

After the reaction is completed, the RMD can be isotated. The isolation of the RMD is usually carried out by means of filtration. In order to reduce the RMD dissolved in the solvent and improve yield, the RMD is preferably precipitated sufficiently by cooling to a temperature ranging from 0° C. to room temperature. In accordance with the aforementioned method, the RMD in high purity can be obtained. In the case in which purity must be further enhanced, purification can be carried out by means of recrystallization.

An RMD is easily decomposed under high temperatures. For this reason, the RMD liquid obtained in accordance with the production method of the first mode of the present invention is provided without isolation to the next step (such as amidization step), and is preferably utilized as it is.

As examples of RMD obtained in the production method of the first mode of the present invention, mention may be made of the compounds represented by formula (1-III):

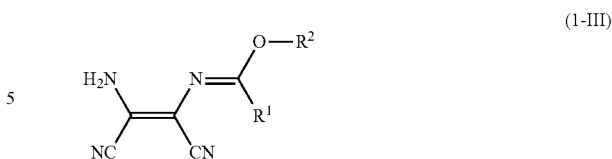

In formula (1-III), $R^1$ is a hydrogen atom, an optionally substituted alkyl group, or an optionally substituted aryl group; and $R^2$ is an optionally substituted alkyl group, or an optionally substituted aryl group.

As examples of the optionally substituted alkyl group or examples of the optionally substituted aryl group in $R^1$ and $R^2$, mention may be made of the same examples as described in the aforementioned $R^1$ in the aforementioned formula (1-II).

Best Modes for Carrying out the Second Modes of the Present Invention

As examples of an N-(2-amino-1,2-dicyanovinyl) formimidate (RMD), mention may be made of compounds represented by formula (2-I). The RMD can be obtained by reacting diaminomaleonitrile (DAMN) and a compound represented by formula (2-III), as described in, for example, Non-Patent Document 2, Patent Document 4, or the like.

$$CH(OR^{11})_3 \quad (2\text{-III})$$

In formula (2-III), each $R^{11}$ is an optionally substituted alkyl group, or an optionally substituted aryl group.

The $R^{11}$ in the formula is an optionally substituted alkyl group, or an optionally substituted aryl group, and as examples thereof, mention may be made of the same groups as defined in $R^1$ in formula (1-II).

In accordance with the production method of the second mode of the present invention, an alcohol ($R^{11}OH$) derived from $R^{11}$ in formula (2-I) and the like are by-produced. In view of easiness of removal of the aforementioned by-products, $R^{11}$ is preferably an alkyl group having 1 to 5 carbon atoms, and a methyl group or an ethyl group is most preferable.

In the production method of the second mode of the present invention, an ether is used as the solvent. As examples of the ether, mention may be made of tetrahydrofuran, dioxane, diethyl ether, diethylene glycol dimethyl ether, and the like. Among these, tetrahydrofuran is preferable.

The reaction between the RMD and ammonia is carried out by adding aqueous ammonia to a solution or suspension of the RMD in ether, or alternatively directly adding the RMD or adding a solution or suspension of the RMD in ether to a liquid containing ether and aqueous ammonia.

Aqueous ammonia is added so that the amount of ammonia preferably ranges from one equivalent to 10 equivalents, and more preferably ranges from 3 to 6 equivalents with respect to the RMD.

The reaction temperature is not particularly limited. If the reaction temperature is remarkably reduced, the reaction slowly proceeds, and a long period of time is needed for production. In contrast, if the reaction temperature is remarkably increased, the amount of the by-products is increased, and purity tends to be reduced. Therefore, the reaction temperature usually ranges from 0 to 50° C. and preferably ranges from 10 to 30° C. In addition, the reaction period is preferably within one hour. If the reaction period is remarkably long, the amount of by-products is increased, and purity tends to be reduced.

After the reaction is completed, AMD-H can be isolated. The isolation of AMD-H is usually carried out by means of filtration. In order to reduce AMD-H dissolved in the solvent and improve yield, AMD-His preferably precipitated sufficiently by cooling to a temperature ranging from 0° C. to room temperature. In accordance with the aforementioned method, AMD-H in high purity can be obtained. In the case in which purity must be further enhanced, purification can be carried out by means of recrystallization.

In the case of providing AMD-H to a cyclization reaction or the like, the AMD-H liquid obtained in accordance with the production method of the second mode of the present invention is provided without isolation to the next step (such as cyclization step), and is preferably utilized as it is.

Best Modes for Carrying Out the Third Modes of the Present Invention $R^{31}$ in formula (3-I) is preferably a hydrogen atom, in view of efficiency of the amidination reaction of step (B). When $R^{31}$ is a methyl group or a phenyl group, a dicyanoimidazole derivative is preferentially produced at the time of the cyclization reaction of step (C).

In accordance with the production method of the third mode of the present invention, an alcohol ($R^{32}OH$) derived from $R^{32}$ in formula (3-I) is by-produced. As $R^{32}$, an alkyl group having 1 to 5 carbon atoms is preferable, and a methyl group or an ethyl group is most preferable, since the alcohol as a by-product is easily removed efficiently.

In step (A), diaminomaleonitrile and the compound represented by formula (3-I) are reacted in the presence of a strong acid to obtain a compound represented by formula (3-II).

The amount of the compound represented by formula (3-I) usually ranges from one equivalent to 2 equivalents, and preferably ranges from 1.05 to 1.3 equivalents with respect to DAMN.

As the strong acid used in step (A), the same strong acid as described in that of the production method of the first mode of the present invention can be mentioned. The usage amount of the strong acid preferably ranges from 0.2 to 0.5% by mol with respect to DAMN. If the amount of the strong acid is increased much, the amount of by-products tends to be increased.

Step (A) is preferably carried out in the presence of an aprotic organic solvent. The aprotic organic solvent is a solvent having no proton-donor properties. The amount of the aprotic organic solvent used in step (A) usually ranges from 0.1 to 1 L, and preferably ranges from 0.1 to 0.3 L with respect to one mol of DAMN. As examples of the aprotic organic solvent, mention may be made of ethers such as tetrahydrofuran, dioxane, diethyl ether, diethylene glycol dimethyl ether, and the like; and ketones such as acetone and the like. Among these, tetrahydrofuran is preferable.

In step (A), a strong acid may be present in the reaction between DAMN and the compound represented by formula (3-I), and the addition order, addition rate and the like of the synthesis raw materials are not particularly limited. In step (A), usually, a solvent is first placed in a reactor, and DAMN and the compound represented by formula (3-I) in specified amounts are together or independently added thereto, followed by adding a strong acid thereto. After the strong acid is added, the reaction system is maintained at a specified temperature, and the reaction proceeds.

The reaction temperature in step (A) is not particularly limited. If the reaction temperature is remarkably reduced, the reaction slowly proceeds, and a long period of time is needed for production. In contrast, if the reaction temperature is remarkably increased, a by-product such as 4,5-dicyanoimidazole or the like is increased, and purity tends to be reduced. Therefore, the reaction temperature usually ranges from room temperature (around 20° C.) to the reflux temperature of the solvent, and preferably ranges from 30 to 50° C. In addition, the reaction period is preferably within one hour. If the reaction period is remarkably long, the amount of by-products is increased, and purity tends to be reduced. The reaction liquid containing the compound represented by formula (3-II) obtained in step (A) can be provided to step (B) as it is.

In step (B), the compound represented by formula (3-II) and a compound represented by the following formula (3-III) are reacted to obtain a compound represented by formula (3-IV) and/or a salt thereof. Step (B) is preferably carried out in the presence of an aprotic organic solvent in the same manner as described in step (A).

$$R^3NH_2 \quad (3\text{-III})$$

In formula (3-III), $R^3$ is independently a hydrogen atom, an optionally substituted alkyl group, or an optionally substituted aryl group. As examples of the optionally substituted alkyl group, or examples of the optionally substituted aryl group in formula (3-III), mention may be made of the same ones as described in $R^1$ in formula (1-II).

In step (B), a solution or suspension of the compound represented by formula (3-II) in an aprotic organic solvent and an aqueous solution of the compound represented by formula (3-III) are mixed, followed by preferably carrying out the reaction while maintaining the reaction system at a specified temperature.

As the solution or suspension of the compound represented by formula (3-II) in an aprotic organic solvent, the reaction liquid obtained in step (A) is used as it is, and thereby, a one-pot synthesis can be carried out.

The aqueous solution of the compound represented by formula (3-III) is added in an amount so that the amount of the compound represented by formula (3-III) preferably ranges from 1 equivalent to 10 equivalents and more preferably ranges from 3 to 6 equivalents with respect to the compound represented by formula (3-II).

As examples of the compound represented by formula (3-III), mention may be made of ammonia; an amine such as methylamine, ethylamine, or the like; an alkanolamine such as methanolamine, ethanolamine, propanolamine, isopropanolamine, or the like; and the like.

The reaction temperature in step (B) is not particularly limited. If the reaction temperature is remarkably reduced, the reaction slowly proceeds, and a long period of time is needed for production. In contrast, if the reaction temperature is remarkably increased, the amount of the by-products is increased, and purity tends to be reduced. Therefore, the reaction temperature usually ranges from 0 to 50° C. and preferably ranges from 10 to 30° C. In addition, the reaction period is preferably within one hour. If the reaction period is remarkably long, the amount of by-products is increased, and purity tends to be reduced. The reaction liquid containing the compound represented by formula (3-IV) and/or a salt thereof obtained in step (B) can be provided to step (C) as it is.

In step (C), the compound represented by formula (3-IV) and/or a salt thereof is cyclized in the presence of a basic aqueous solution. Step (C) is carried out in the presence of an aprotic organic solvent. By means of the aforementioned cyclization reaction, a compound represented by formula (3-V) can be obtained.

The basic aqueous solution is obtained by dissolving a basic compound in water. As examples of the basic compound, mention may be made of alkali metal hydroxides such as sodium hydroxide, potassium hydroxide, and the like; ammonia, amine; and the like. Among these, an alkali metal hydroxide is preferable.

The basic aqueous solution is added in an amount so that the amount of the basic compound preferably ranges from one equivalent to 3 equivalents, and more preferably ranges from 1.5 to 2.5 equivalents with respect to the compound represented by formula (3-IV) and/or a salt thereof, and when the reaction temperature in step (C) preferably ranges from 0 to 50° C. and more preferably ranges from 0 to 30° C., the cyclization reaction proceeds. Thereby, a derivative (AICN) in which $R^4$ is —CN can be obtained.

The basic aqueous solution is added in an amount so that the amount of the basic compound preferably ranges from 3 to 5 equivalents with respect to the compound represented by formula (3-IV) and/or a salt thereof, and when the reaction temperature in step (C) is specified to the reflux temperature of the solvent, the cyclization and hydrolysis reaction proceeds. Thereby, a derivative (AICA) in which $R^4$ is —$CONH_2$ can be obtained.

After step (C) is completed, the compound represented by formula (3-V) can be purified. As an example of purification methods, mention may be made of, for example, an acid such as hydrochloric acid is added to the reaction liquid obtained in step (C) to form a hydrochloride salt or the like, and extraction or concentration is carried out. In addition, as described in Japanese Unexamined Patent Application, First Publication No. 2004-75610, a depigmentation treatment method in which a depigmentation agent such as activated carbon or the like is added to the aforementioned extraction can be mentioned.

As examples of the optionally substituted alkyl group, or the optionally substituted aryl group in $R^1$ and $R^3$ of formula (3-V), the same ones as described in $R^1$ of the aforementioned formula (1-II) may be mentioned.

The compounds represented by formula (3-V) obtained by the production method of the third mode of the present invention, and in particular, 5-amino-1H-imidazole-4-carboxamide or 5-amino-1H-imidazole-4-carbonitrile can be utilized as materials of intermediates for producing dacarbazine and temozoromide of antineoplastic drugs, and urazamide of a hepatoprotective drug.

EXAMPLES

Examples of the First Modes of the Present Invention

Next, the first mode of the present invention is described in detail with reference to Examples and Comparative Examples. It should be understood that the first mode of the present invention is not limited to these Examples.

Example 1-1

Methanol, in an amount of 216 mL, was placed in a four-necked flask with a volume of 500 mL, and 108.1 g (purity: 98.7%, 0.987 mol) of DAMN and 116.73 g (1.100 mol) of trimethyl orthoformate were added thereto. p-Toluenesulfonic acid, monohydrate, in an amount of 190 mg, was added to the aforementioned mixture, and the reaction mixture was stirred while maintaining the temperature at 65° C. 45 minutes after stirring was started, crystals of MMD were precipitated, and completion of the reaction was suggested.

After the reaction mixture was stirred for 1.5 hours, the reaction mixture was cooled to 5° C. The crystals were filtered and washed with 100 mL of cooled methanol, followed by drying. Thereby, 118.56 g (0.852 mol, yield=80%) of methyl N-(2-amino-1,2-dicyanovinyl)formimidate (MMD) was obtained.

Example 1-2

Methanol, in an amount of 20 mL, was placed in a four-necked flask with a volume of 100 mL, and 10.95 g (purity: 98.7%, 0.100 mol) of DAMN and 12.73 g (0.120 mol) of trimethyl orthoformate were added thereto. Trifluoroacetic acid, in an amount of about 20 mg, was added to the aforementioned mixture, and the reaction mixture was stirred while maintaining the temperature at 40° C. 5 minutes after stirring was started, crystals of MMD were precipitated, and completion of the reaction was suggested.

The reaction product had the same peak pattern as that of standard MMD in a reversed-phase HPLC analysis.

After the reaction mixture was stirred for one hour, 20 mL of methanol was added thereto and the reaction mixture was cooled to not more than 5° C. Thereby, crystals were precipitated. The crystals were filtered and washed with 20 mL of cooled methanol, followed by drying. Thereby, 10.21 g (0.0680 mol, yield=68%) of MMD was obtained.

Example 1-3

Tetrahydrofuran (THF), in an amount of 20 mL, was placed in a four-necked flask with a volume of 100 mL, and 10.95 g (purity: 98.7%, 0.100 mol) of DAMN and 12.73 g (0.120 mol) of trimethyl orthoformate were added thereto. Methanesulfonic acid, in an amount of about 20 mg, was added to the aforementioned mixture, and the reaction mixture was stirred while maintaining the temperature at 40° C. 10 minutes after stirring was started, crystals of MMD were precipitated, and completion of the reaction was suggested.

The reaction product had the same peak pattern as that of standard MMD in a reversed-phase HPLC analysis.

Example 1-4

THF, in an amount of 20 mL, was placed in a four-necked flask with a volume of 100 mL, and 10.81 g (purity: 98.7%, 0.987 mol) of DAMN and 16.52 g (0.156 mol) of trimethyl orthoformate were added thereto. Condensed sulfuric acid, in an amount of about 20 mg, was added to the aforementioned mixture, and the reaction mixture was stirred while maintaining the temperature at 50° C. 30 minutes after stirring was started, a reversed-phase HPLC analysis was carried out. As a result, the reaction product had the same peak pattern as that of standard MMD.

Example 1-5

Methanol, in an amount of 20 mL, was placed in a four-necked flask with a volume of 100 mL, and 10.95 g (purity: 98.7%, 0.100 mol) of DAMN and 14.42 g (0.120 mol) of trimethyl orthoacetate were added thereto. Methanesulfonic acid, in an amount of about 20 mg, was added to the aforementioned mixture, and the reaction mixture was stirred while maintaining the temperature at 40° C. After methanesulfonic acid was added, crystals of methyl N-(2-amino-1,2-dicyanovinylacetimidate (Me-MMD) were gradually precipitated. 30 minutes after stirring was started, a reversed-phase HPLC analysis was carried out. As a result, the peak area of DAMN was 0.1%.

After the reaction mixture was stirred for one hour, 10 mL of methanol was added thereto and the reaction mixture was cooled to 5° C. Thereby, crystals were precipitated. The crystals were filtered and then dried. Thereby, 11.64 g (0.071 mol, yield=71%) of Me-MMD was obtained.

Comparative Example 1-1

THF, in an amount of 15 mL, was placed in a four-necked flask with a volume of 100 mL, and 10.81 g (purity: 98.7%, 0.0987 mol) of DAMN and 16.52 g (0.155 mol) of trimethyl orthoformate were added thereto. The reaction mixture was stirred for 2.5 hours while maintaining the temperature at 65° C. According to a reversed-phase HPLC analysis, no peak of MMD could be confirmed.

Comparative Example 1-2

THF, in an amount of 20 mL, was placed in a four-necked flask with a volume of 100 mL, and 10.81 g (purity: 98.7%, 0.0987 mol) of DAMN and 11.67 g (0.110 mol) of trimethyl orthoformate were added thereto. After about 20 mg of acetic acid was added to the reaction mixture, the reaction mixture was stirred for 30 minutes while maintaining the temperature at 50° C. According to a reversed-phase HPLC analysis, no peak of MMD could be confirmed.

Examples of the Second Modes and the Third Modes of the Present Invention

The second mode and the third mode of the present invention are further described in detail with reference to Examples and Comparative Examples. It should be understood that the second modes of the present invention are not limited to the Examples.

Example 2-1

Tetrahydrofuran (THF), in an amount of 400 mL, was placed in a four-necked flask with a volume of 3 L, and 219.1 g (purity: 98.7%, 2.00 mol) of DAMN and 254.7 g (2.40 mol) of trimethyl orthoformate were added thereto. 480 mg of methanesulfonic acid was added to the aforementioned mixture, and the reaction mixture was stirred for one hour while maintaining the temperature at 40° C. Thereby, a slurry of MMD was obtained.

THF, in an amount of 200 mL, was added to the aforementioned slurry of MMD, followed by adding 545.0 g (8.0 mol) of 25% aqueous ammonia thereto. The reaction mixture was stirred for one hour while maintaining the temperature at 30° C. Thereby, a slurry of AMD-H was obtained.

As a result of analysis of the aforementioned slurry of AMD-H by means of HPLC, 3% of AICN, 82% of AMD-H and 9% of an intermediate represented by the following formula (2-IV) were obtained in view of area ratio.

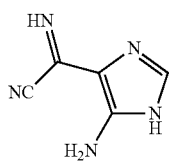

(2-IV)

Subsequently, 640.0 g (4.0 mol) of a 25% aqueous solution of sodium hydroxide was added to the aforementioned slurry of AMD-H. The reaction mixture was stirred for one hour while maintaining the temperature at 30 to 40° C.

From the obtained reaction liquid, the ammonia was removed by distillation under reduced pressure, and 560 g (5.4 mol) of a 35% aqueous solution of hydrochloric acid was added thereto to adjust the pH to 6. The precipitated black insoluble products were removed by filtration.

Subsequently, 1.2 L of THF was added thereto, and an extraction operation of AICN was repeated three times. As a result of quantitative analysis of AICN in the THF extraction, the content of AICN was 169 g (1.56 mol).

The aforementioned THF extraction was concentrated, followed by adding water and removing THF by distillation. Thereby, an aqueous solution of AICN was obtained. Activated carbon, in an amount of 40 g, was added to the aforementioned aqueous solution, and the mixture was stirred for 30 minutes at 50° C. The activated carbon was removed by filtration, and water was added to the obtained filtrate so that the weight of the filtrate was 1,000 g. The aforementioned liquid was gradually cooled. Crystals were precipitated by stirring the liquid for 30 minutes while maintaining the temperature to 0 to 5° C., and the aforementioned crystals were obtained by filtration. The crystals were washed with 300 mL of cooled water, and were dried under reduced pressure at 40 to 50° C. Thereby, crystals of AICN were obtained in an amount of 146.2 g (purity=98.1%, yield=66.4%).

Example 2-2

THF, in an amount of 20 mL, was placed in a four-necked flask with a volume of 200 mL, and 10.95 g (purity: 98.7%, 0.100 mol) of DAMN and 12.73 g (0.120 mol) of trimethyl orthoformate were added thereto. 27 mg of methanesulfonic acid was added to the aforementioned mixture, and the reaction mixture was stirred for one hour while maintaining the temperature at 40° C. Thereby, a slurry of MMD was obtained.

THF, in an amount of 15 mL, was added to the aforementioned slurry of MMD, followed by adding 27.25 g (0.400 mol) of 25% aqueous ammonia thereto. The reaction mixture was stirred for one hour while maintaining the temperature at 30° C. Thereby, a slurry of AMD-H was obtained.

A 25% aqueous solution of sodium hydroxide, in an amount of 32.00 g (0.200 mmol), was added to the slurry of AMD-H. The reaction mixture was stirred for one hour at 30 to 40° C.

A 35% aqueous solution of hydrochloric acid, in an amount of 20.8 g (0.20 mol), was added to the obtained reaction liquid. As a result of quantitative analysis of AICN in the solution, AICN was contained in an amount of 9.43 g (0.0872 mol).

Comparative Example 2-1

AMD-H was tried to be obtained in the same manner as described in Example 2-1, with the exception of blowing an ammonia gas instead of addition of aqueous ammonia. However, AMD-H was precipitated at a blowing inlet for ammonia gas, and the blowing inlet was closed. Thereby, the reaction could not be continued.

Comparative Example 2-2

MMD, in an amount of 3.00 g (20 mmol), and 10 mL of methanol were placed in a four-necked flask with a volume of 100 mL. Thereby, a slurry of MMD was obtained.

A methanol solution in which 1.77 g (100 mmol) of ammonia was dissolved in 10 mL of methanol was added to the aforementioned slurry of MMD. The mixture was stirred for 3 hours at room temperature. Thereby, a slurry of AMD-H was obtained. As a result of HPLC analysis of the aforementioned slurry of AMD-H, purity of AMD-H in view of area ratio was 92%.

A 25% aqueous solution of sodium hydroxide, in an amount of 3.20 g (20 mmol) was added to the slurry of AMD-H. The mixture was stirred for 20 hours at room temperature. Thereby, a reaction liquid of AICN was obtained. As a result of HPLC analysis of the reaction liquid, in view of area ratio, 46% of AICN, 14% of DC, and 35% of AIC-imidate represented by the following formula (2-V) were obtained.

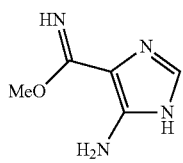

(2-V)

From the aforementioned results, it can be seen that when AMD-H obtained by the reaction with aqueous ammonia in ether is used in accordance with the second mode and the third mode of the present invention, yield of the cyclization reaction is enhanced, and AICN with high purity can be obtained. In contrast, it can be seen that when AMD-H obtained by the reaction with ammonia in an alcohol, side reactions during the cyclization reaction are increased, and yield of AICN is poor.

Example 3-1

A slurry of MMD was obtained in the same manner as described in Example 2-1. (R)-2-amino-1-methylethanol, in an amount of 4.89 g (0.066 mol), was added to the aforementioned slurry of MMD (MMD=9.0 g (0.06 mol), THF=60 mL) at 5° C. The mixture was stirred for 4 hours at 5 to 10° C. Thereby, a liquid of a compound represented by the following formula (3-IVa) was obtained.

Subsequently, 14.4 g (90 mmol) of a 25% aqueous solution of sodium hydroxide was added dropwise thereto over 10 minutes at 10° C. After completion of the addition, the mixture was stirred for 18 hours at 10° C. A 35% aqueous solution of hydrochloric acid, in an amount of 11.8 g (0.11 mol), was added to the obtained reaction liquid, and the mixture was stirred for 30 minutes. As a result of HPLC analysis of the reaction liquid, AICN—(R)HP represented by the following formula (3-Va) was contained in 82% in view of area ratio.

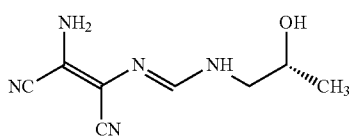

(3-IVa)

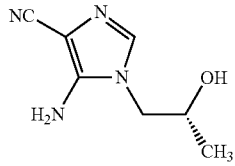

(3-Va)

Example 3-2

A compound represented by the following formula (3-IVb) and AICN—(S)HP represented by the following formula (3-Vb) were obtained in the same manner as described in Example 3-1 with the exception of replacing (R)-2-amino-1-methylethanol with (S)-2-amino-1-methylethanol. As a result of an HPLC analysis, AICN—(S)HP represented by the following formula (-Vb) was contained in 90.2% in view of area ratio.

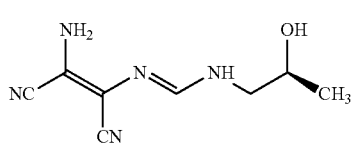

(3-IVb)

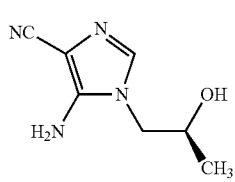

(3-Vb)

The invention claimed is:

1. A method for producing N-(2-amino-1,2-dicyanovinyl)formamidine, comprising the steps of reacting an N-(2-amino-1,2-dicyanovinyl)formimidate and ammonia by adding aqueous ammonia to a solution or suspension of an N-(2-amino-1,2-dicyanovinyl)formimidate in ether, or alternatively directly adding an N-(2-amino-1,2-dicyanovinyl)formimidate or adding a solution or suspension of an N-(2-amino-1,2-dicyanovinyl)formimidate in ether to a liquid containing ether and aqueous ammonia.

2. The method for producing N-(2-amino-1,2-dicyanovinyl)formamidine according to claim 1, wherein the aforementioned ether is tetrahydrofuran.

* * * * *